United States Patent
Yaku et al.

(10) Patent No.: US 7,521,214 B2
(45) Date of Patent: Apr. 21, 2009

(54) METHOD OF IMMOBILIZING MALATE DEHYDROGENASE ON A SUBSTRATE

(75) Inventors: Hidenobu Yaku, Osaka (JP); Hirokazu Sugihara, Kanagawa (JP)

(73) Assignee: Panasonic Corporation, Osaka (JP)

( * ) Notice: Subject to any disclaimer, the term of this patent is extended or adjusted under 35 U.S.C. 154(b) by 16 days.

(21) Appl. No.: 11/976,951

(22) Filed: Oct. 30, 2007

(65) Prior Publication Data
US 2008/0050765 A1 Feb. 28, 2008

Related U.S. Application Data

(63) Continuation of application No. PCT/JP2007/058465, filed on Apr. 18, 2007.

(30) Foreign Application Priority Data
May 11, 2006 (JP) .............................. 2006-133039

(51) Int. Cl.
*G01N 33/53* (2006.01)
*C12N 11/00* (2006.01)
*C12N 11/14* (2006.01)
*C12N 11/02* (2006.01)
*C12N 11/08* (2006.01)

(52) U.S. Cl. ...................... 435/174; 435/7.1; 435/176; 435/177; 435/180

(58) Field of Classification Search ................. None
See application file for complete search history.

(56) References Cited

FOREIGN PATENT DOCUMENTS

| JP | 55-13860 | 1/1980 |
|---|---|---|
| JP | 59-166084 | 9/1984 |
| JP | 2-62952 | 3/1990 |
| JP | 2-96649 | 4/1990 |
| JP | 2-096649 A | 4/1990 |
| JP | 9-297121 | 11/1997 |
| JP | 2004-24254 | 1/2004 |

OTHER PUBLICATIONS

Tsukatani, T., et al., "Quantification of $_L$-Tartrate in Wine by Stopped-Flow Injection Analysis Using Immobilized $_D$-Malate Dehydrogenase and Fluorescence Detection", Analytical Sciences, Mar. 2000, pp. 265-268, vol. 16, The Japan Society for Analytical Chemistry.

Hatley, R.H., et al., "Variation in Apparent Enzyme Activity in Two-Enzyme Assay Systems: Phosphoenolpyruvate Carboxylase and Malate Dehydrogenase", Biotechnology and Applied Biochemistry, 1989, pp. 367-370, vol. 11, Academic Press, Inc.

Salvarrey, M.S., et al., "Some properties of the NADP-specific malic enzyme from the moderate halophile *Vibrio costicola*", Can. J. Microbiol., 1980, pp. 50-57, vol. 26, National Research Council of Canada.

*Primary Examiner*—David M Naff
(74) *Attorney, Agent, or Firm*—McDermott Will & Emery LLP

(57) ABSTRACT

Immobilization of malate dehydrogenase on a substrate using a glycerol solution containing malate dehydrogenase is achieved through dropping a mixed solution obtained by adding at least one selected from malic acid and malate to the glycerol containing malate dehydrogenase on the substrate, and drying it thereon. It is preferable to prepare the mixed solution by adding the malate to the glycerol solution containing malate dehydrogenase. The malate is preferably at least one selected from potassium malate and sodium malate.

3 Claims, 7 Drawing Sheets

METHOD OF IMMOBILIZING MALATE DEHYDROGENASE ON A SUBSTRATE

RELATED APPLICATIONS

This Application is a continuation of International Application No. PCT/JP2007/058465, whose international filing date is Apr. 18, 2007 which in turn claims the benefit of Japanese Patent Application No. 2006-133039, filed on May 11, 2006, the disclosures of which Applications are incorporated by reference herein. The benefit of the filing and priority dates of the International and Japanese Applications is respectfully requested.

TECHNICAL FIELD

The present invention relates to a method of immobilizing malate dehydrogenase on a substrate, particularly to a method of immobilizing malate dehydrogenase contained in a glycerol solution on a substrate.

BACKGROUND ART

An immunoassay is a method of measuring the amount of target substances making use of the affinity between an antigen and an antibody, namely an antigen-antibody reaction. The antigen-antibody reaction exhibits the highest discriminably of target substances and has the most variety among biological phenomena known conventionally. For this reason, much attention is drawn to the immunoassay that enables direct measurement of target substances from a biological sample including a large variety of biomolecules without isolating and purifying the target substances.

FIG. 1 is a flow diagram for explaining one example of immunoassays. First, a sample solution 5 containing target substances 4 is added into a chamber 1 to which antibodies 2 are fixed (A1). Since each antibody 2 has an antigen-binding site for the target substances 4, the addition causes antigen-antibody reactions between the target substances 4 and the antibodies 2. Next, the chamber 1 is washed using a solution such as a buffer solution (A2). Impurities 3 possibly contained in the sample solution are removed from the chamber 1. Second antibodies 7 are then added into the chamber 1 (A3). Each second antibody 7 has an antigen-biding site that is not identical to the site of each antibody 2. The addition of the second antibodies 2 causes antigen-antibody reactions between the target substances 4 bound to the antibodies 2 and the second antibodies 7. Each second antibody 7 is labeled with a known labeling substance 6 such as a fluorescent substance, a radioactive substance and an enzyme. The chamber 1 is then washed again using a solution such as a buffer solution (A4) for removing second antibodies 7 that are not bound to the target substances 4 from the chamber 1. The amount of the target substances 4 is then calculated by measuring the amount of complexes, each composed of the antibody 2, the target substance 4 and the second antibody 7, remained in the chamber 1, more specifically, the amount of the labeling substances 6 labeling the second antibodies 7 of the complexes (A5).

FIG. 2 is a flow diagram for explaining another example of immunoassays. In this example, a solution containing labeled target substances 4b at a predetermined concentration is added with a sample solution containing target substances 4a into the chamber 1 (B1). The labeled target substances are mimic targets and each labeled target substance has an epitope identical to epitopes of the target substances 4a and is labeled with the labeling substance 6. The addition causes competitive antigen-antibody reactions are progressed in the chamber 1 between the antibodies 2 and the target substances 4a and between the antibodies 2 and the labeled target substances. The chamber 1 is then washed using a solution such as a buffer solution (B2) for removing substances such as impurities 3 possibly contained in the sample solution and unreacted labeled target substances from the chamber 1. The amount of the target substances 4a is then calculated by measuring the amount of the labeled target substances added into the chamber and the amount of complexes, composed of the antibody 2 and the labeled target substance, remained in the chamber 1, more specifically, the amount of the labeling substances 6 labeling the labeled target substances of the complexes (B3).

The immunoassay is not limited to the two examples mentioned above, and also can be performed by other assaying methods. The amount of the target substances in the sample solution is calculated on the basis of the amount of the labeling substances that reflects the amount of the target substances in any assaying method. Examples of the method of measuring the amount of the labeling substances include a method using a means of measuring the amount optically. This method requires a light source and a fluorescence detector as described in the following paper: Tadayuki Tsukatani and Kiyoshi Matsumoto, "Quantification of L-Tartrate in Wine by Stopped-Flow Injection Analysis Using Immobilized D-Malete Dehydrogenase and Fluorescence Detection", Analytical Sciences, March 2000, vol. 16, pp. 265-268, and a device for the optical measurement is not easy to downsized and downscaled.

Much attention is drawn to a method employing an electrochemical means from the viewpoint of downsizing and downscaling a measurement device employed in the immunoassays as well as performing the assays in safety, easily and with high accuracy. JP 2(1990)-62952A and JP 9(1997)-297121A, for example, disclose a biosensor for measuring the amount of target substances in a sample making use of an enzymatic cycling reaction system that employs alkaline phosphatase as a labeling substance and potassium hexacyanoferrate(III) (potassium ferricyanide) as an electron mediator.

FIG. 3 is a diagram for explaining the enzymatic cycling reaction system employed in biosensors of JP 2(1990)-62952A and JP 9(1997)-297121A. This enzymatic cycling reaction system is composed of first to third reactions induced in a reaction solution containing alkaline phosphatase, oxidized nicotinamide adenine dinucleotide phosphate (NADP), ethanol, alcohol dehydrogenase, diaphorase, and potassium ferricyanide that is to be a substrate of diaphorase. In the first reaction, NADP is dephosphorylated by alkaline phosphatase and then converted into oxidized nicotinamide adenine dinucleotide (NAD). In the second reaction, a redox reaction through catalysis of alcohol dehydrogenase reduces the first reaction induced-NAD into reduced nicotinamide adenine dinucleotide (NADH) and oxidizes ethanol into acetaldehyde. In the third reaction, the second reaction-induced NADH is oxidized by potassium ferricyanide through catalysis of diaphorase and then converted into NAD, and the potassium ferricyanide is converted into potassium hexacyanoferrate(II) (potassium ferrocyanide). NADP may be replaced with reduced nicotinamide adenine dinucleotide phosphate (NADPH). Voltage application to the reaction solution converts the potassium ferrocyanide into potassium ferricyanide. Since the first to the third reactions are progressed in the reaction solution, the amount of the potassium ferrocyanide generated by the third reaction reflects the amount of the alkaline phosphatase contained in the reaction solution. The amount of the alkaline phosphatase is thus measured through a measurement of the amount of an oxidation current generated by the conversion from the potassium ferrocyanide into the potassium ferricyanide.

Long-term retainment of reagents involved in enzymatic cycling reactions in a chip is significant to provide a biosensor chip. The enzymatic cycling reaction system using alcohol dehydrogenase requires ethanol as mentioned above. Ethanol is not easily retained in the chip for a long time due to the high volatility. For this reason, a biosensor chip is not realized easily with the enzymatic cycling reaction system employing alcohol dehydrogenase.

DISCLOSURE OF INVENTION

The present inventor has established a novel enzymatic cycling reaction system not requiring a high volatile reagent. FIG. 4 is a diagram for explaining the novel enzymatic cycling reaction system. The primary reaction mechanism of this system is identical to that of the enzymatic cycling reaction system illustrated in FIG. 3. This novel enzymatic cycling reaction system employees malate dehydrogenase instead of the alcohol dehydrogenase, and at least one selected from malic acid and malate instead of ethanol. This novel enzymatic cycling reaction system is free from a high volatile reagent such as ethanol.

Retaining reagents that compose an enzymatic cycling reaction system crashworthy in a chip is significant to provide a biosensor chip. The reagents should be retained at a strength that allows the reagents to be kept at their immobilized position even after somewhat strong shocks are applied to the chip during storage.

Malate dehydrogenase is immobilized in the chip preferably use a stock solution that is a glycerol solution dissolves malate dehydrogenase. This is because the glycerol solution containing malate dehydrogenase exhibits less inactivation of malate dehydrogenase than other stock solutions such as a 3.2M ammonium sulfate solution containing malate dehydrogenase.

Due to the difficulty of drying the glycerol solution containing malate dehydrogenase, this solution has a problem of keeping high fluidity even after an adequate drying. For this reason, malate dehydrogenase is not easily immobilized in the chip with the glycerol solution.

The present invention is intended to provide a method of immobilizing malate dehydrogenase on a substrate using a glycerol solution containing malate dehydrogenase.

In a development of a biosensor chip using the enzymatic cycling reaction system illustrated in FIG. 4, the present inventor found that an addition of at least one selected from malic acid and malate to a glycerol solution containing malate dehydrogenase enables the glycerol solution to be easily dried, and the method of the present invention was completed. The present invention provides a method of immobilizing malate dehydrogenase on a substrate. The method includes placing a mixed solution on a substrate, and drying the mixed solution to immobilize malate dehydrogenase on the substrate. The mixed solution is obtained by adding at least one selected from malic acid and malate to a glycerol containing malate dehydrogenase.

DESCRIPTION OF THE PREFERRED EMBODIMENTS

As mentioned above, a glycerol solution containing malate dehydrogenase is not easily dried on a substrate. However, the present inventor found that an addition of at least one selected from malic acid and malate to the glycerol solution enables the glycerol solution to be dried and immobilized on a substrate. With reference to various experimental results, the addition of the other reagents that compose the enzymatic cycling reaction system illustrated in FIG. 4 such as potassium ferricyanide, diaphorase, NADP and NADPH does not enable a glycerol solution containing malate dehydrogenase to be easily dried as described below.

Malate is preferably added to a glycerol solution containing malate dehydrogenase. This is because the malate dehydrogenase can be immobilized on a substrate without depressing its activity as described in the Examples below. Examples of the malate include at least one selected from potassium malate and sodium malate. In the method of the present invention, in addition to at least one selected from potassium malate and sodium malate, the other reagents that compose the enzymatic cycling reaction system illustrated in FIG. 4 may be added as an additive to a glycerol solution containing malate dehydrogenase as long as the glycerol solution can be dried and immobilized on a substrate.

Examples of material for the substrate include polyethylene terephthalate (PET). The material for the substrate may be selected from glass and resins other than PET such as polycarbonate, polyimide and polypropylene.

A mixed solution obtained by adding at least one selected from malic acid and malate to a glycerol containing malate dehydrogenase may be placed on a substrate by known methods as dropping, coating and spraying.

Drying the mixed solution on the substrate may be performed by vacuum drying the substrate that has the mixed solution placed thereon at room temperature (25° C.) for about two hours. Conditions of the drying operation may be modified as long as the malate dehydrogenase is immobilized on the substrate. The modification of the conditions should be limited to such an extent that the malate dehydrogenase is not inactivated by the drying.

According to the method of the present invention, malate dehydrogenase can be immobilized on a substrate at a strength that allows the malate dehydrogenase to be kept at its immobilized position even after somewhat strong shocks are applied to the substrate. As described in the Examples below, malate dehydrogenase is highly immobilized on a substrate, and is easily dissolved in a solvent typically as a sample solution.

Figure 4:
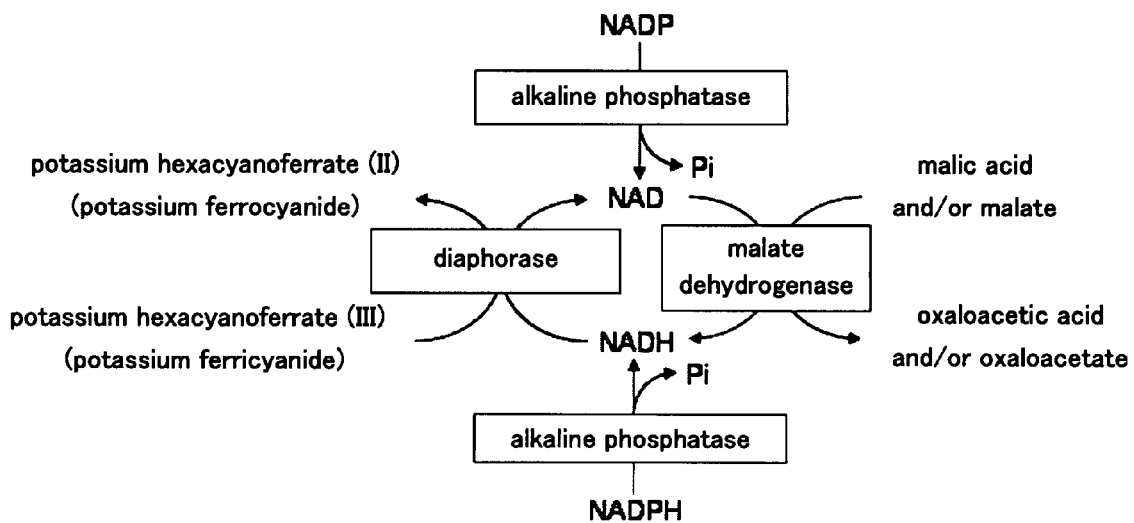
FIG. 4 is a diagram for explaining the novel enzymatic cycling reaction system.
Figure 5:
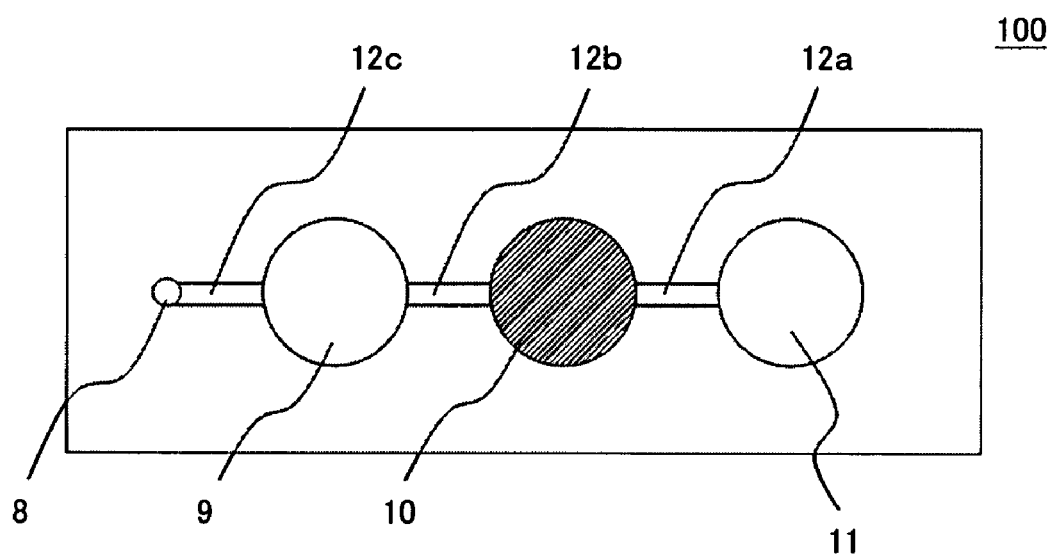
FIG. 5 is a diagram illustrating one example of the chips for performing the immunoassays.
Figure 6:
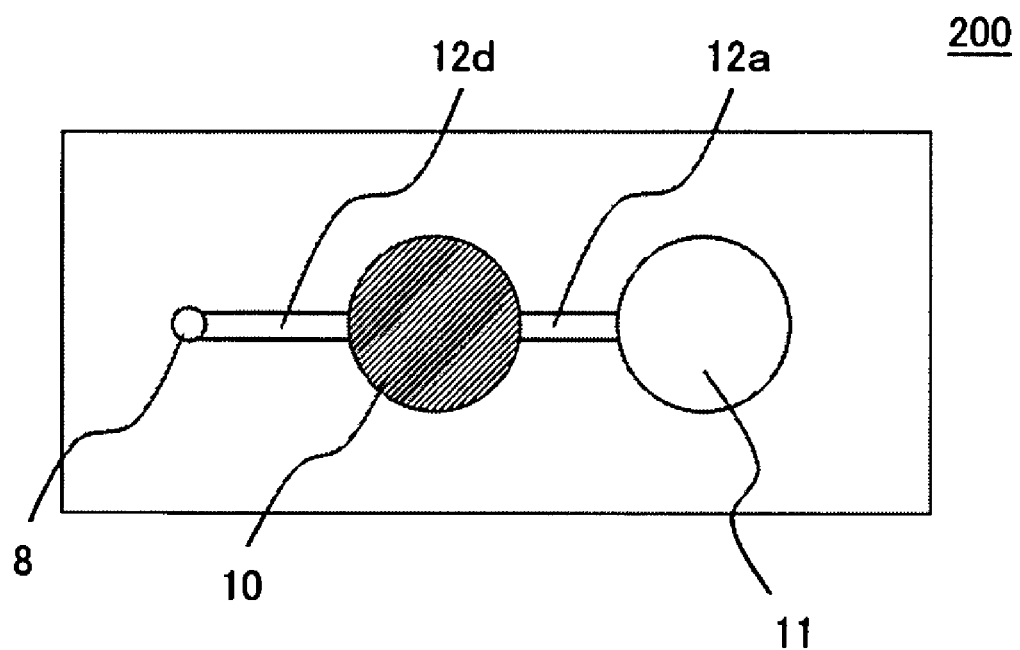
FIG. 6 is a diagram illustrating another example of the chips for performing the immunoassays.

FIGS. 5 and 6 are diagrams for explaining examples of chips for measuring the amount of target substances in a sample solution using the enzymatic cycling reaction system illustrated in FIG. 4.

As illustrated in FIG. 5, a chip 100 includes: an injection port 8 through which a sample solution is introduced into the chip; a reaction chamber 9 in which a solution containing alkaline phosphatase labeled substances, the amount of which reflects the amount of the target substances in the sample solution, is obtained; a reagent immobilized chamber 10; and an electrode chamber 11 in which electrodes for potentiometry are retained. The reagent immobilized chamber 10 and the electrode chamber 11 are connected to each other through a channel 12a. The reaction chamber 9 and the reagent immobilized chamber 10 are connected to each other through a channel 12b. The injection port 8 and the reaction chamber 9 are connected to each other through a channel 12c. As illustrated in FIG. 6, a chip 200 includes an injection port 8, a reagent immobilized chamber 10 and an electrode chamber 11. The reagent immobilized chamber 10 and the electrode chamber 11 are connected to each other through the channel 12a. The injection port 8 and the reaction chamber 9 are connected to each other through a channel 12d.

Malate dehydrogenase, at least one selected from malic acid and malate, NADP and/or NADPH, potassium ferricyanide, and diaphorase are immobilized in the reagent immobilized chamber 10. The reagents mentioned above, from malate dehydrogenase to diaphorase, are in a state of being able to be dissolved in a sample solution, which is to be introduced into the reagent immobilized chamber 10. As mentioned above, malate dehydrogenase may be immobilized on the substrate of the chip through the placement and the drying of the mixed solution thereon. The mixed solution is obtained by adding at least one selected from malic acid and malate to a glycerol containing malate dehydrogenase. NADP and/or NADPH, potassium ferricyanide, and diaphorase can be immobilized easily on the substrate of the chip by placing and drying them thereon.

Figure 1:
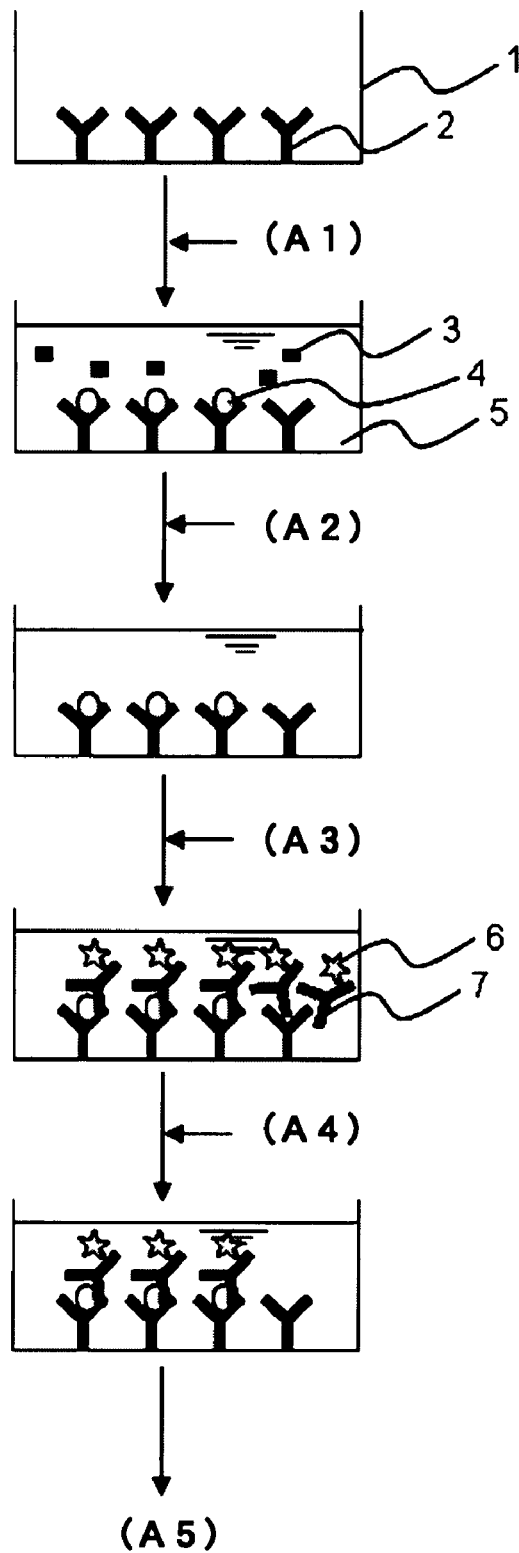
FIG. 1 is a flow diagram for explaining one example of immunoassays.
Figure 2:
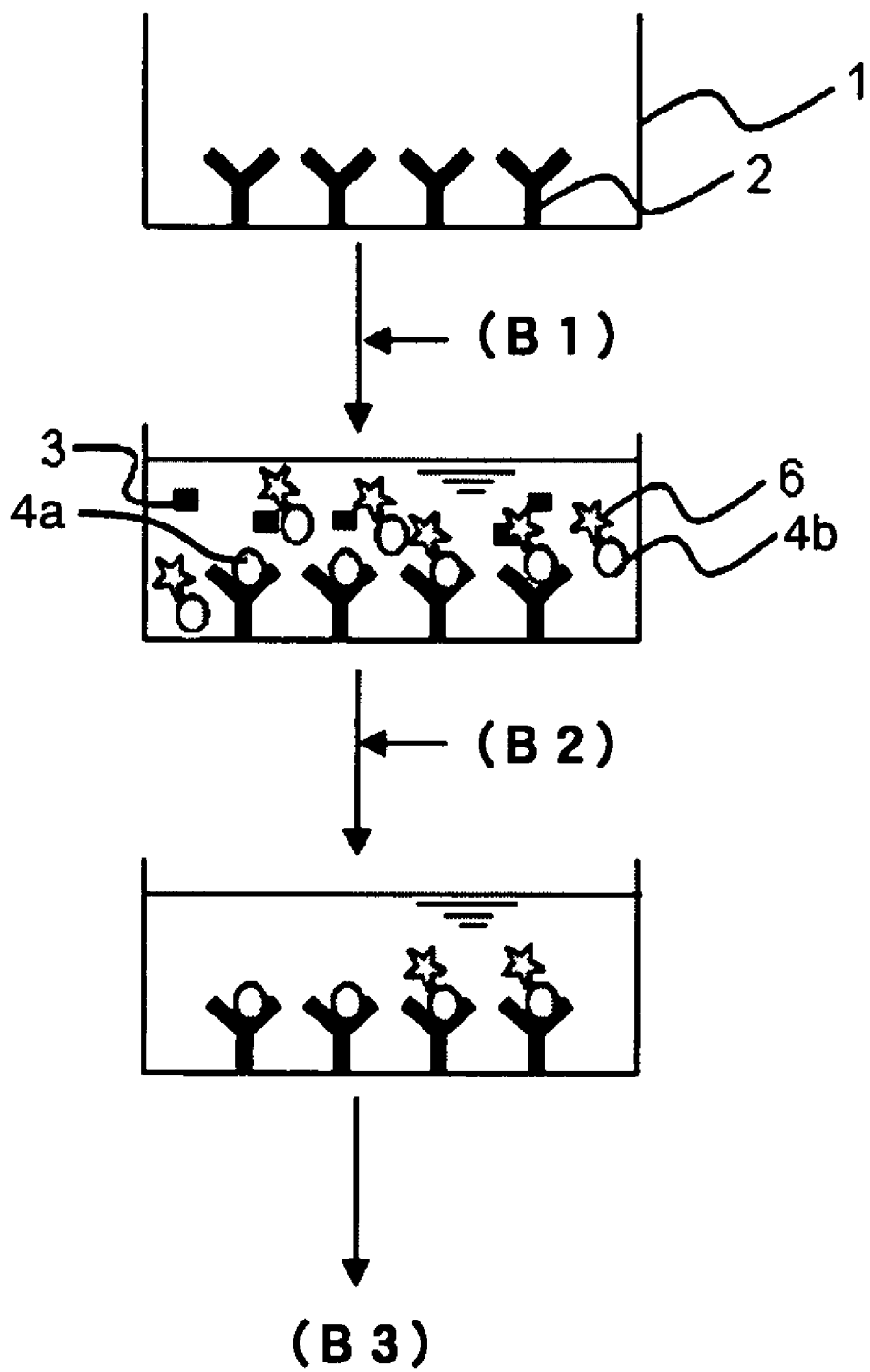
FIG. 2 is a flow diagram for explaining another example of immunoassays.
Figure 3:
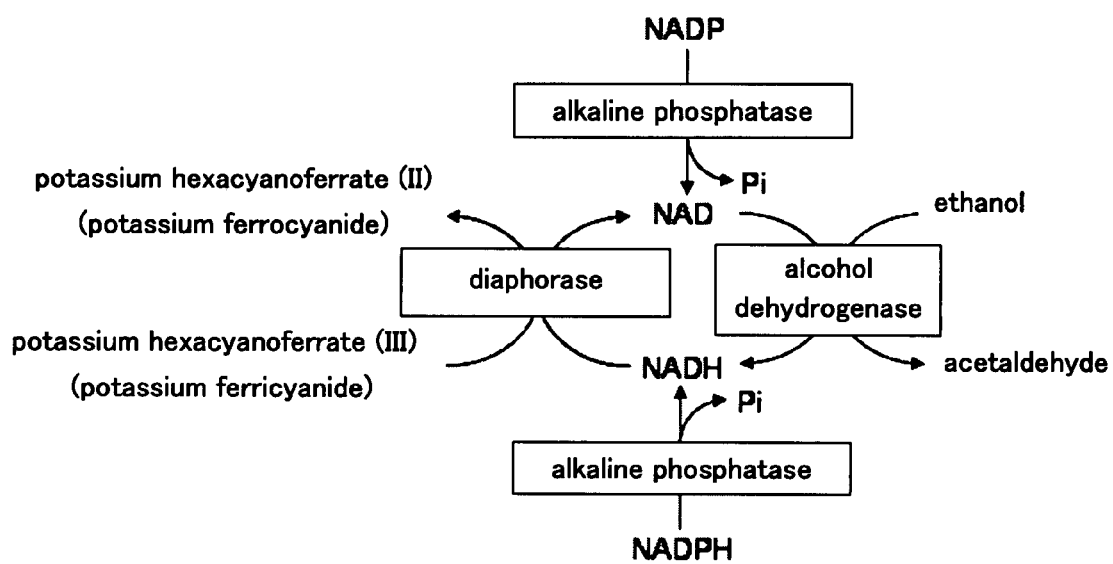
FIG. 3 is a diagram for explaining the enzymatic cycling reaction system using alcohol dehydrogenase.

In the chip 100, a sample solution introduced from the injection port 8 is sent to the reaction chamber 9 through the channel 12c. A solution containing alkaline phosphatase labeled substances, the amount of which reflects the amount of target substances in the sample solution, is prepared in the reaction chamber 9. This solution is then sent to the reagent immobilized chamber 10 through the channel 12b. Examples of reactions for obtaining this solution include various series of reactions illustrated in the flow diagrams of FIGS. 1 and 2. The number and arrangement of chambers and channels composing the reaction chamber 9 can be determined based on reactions to be caused in the reaction chamber 9.

In the chip 200, a solution containing alkaline phosphatase labeled substances, the amount of which reflects the amount of target substances in a sample solution, is introduced to the reagent immobilized chamber 10 from the injection port 8 through the channel 12d. The solution containing the alkaline phosphatase labeled substances is prepared by a chip user before the introduction.

In the chips 100 and 200, introduction of the solution containing alkaline phosphatase labeled substances to the reagent immobilized chamber 10 causes dissolution of the reagents mentioned above, from malate dehydrogenase to diaphorase, in the solution. In the reagent immobilized chamber 10, the cycling reaction illustrated in FIG. 4 is then progressed among the alkaline phosphatase in the solution and the reagents. The solution is sent to the electrode chamber 11 through the channel 12a. In the electrode chamber 11, voltage application to the solution is performed to convert potassium ferrocyanide obtained through the cycling reaction to potassium ferricyanide. The amount of current generated by the conversion is measured (potentiometry). The amount of the target substances in the sample solution is calculated by measuring the amount of the current obtained through the potentiometry.

The reagents mentioned above, from malate dehydrogenase to diaphorase, may be immobilized in the channels 12a, 12b, 12d and the electrode chamber 11 instead of the reagent immobilized chamber 10 at a state of being able to be dissolved in a solution typically as a sample solution. The electrode chamber 11 may have an electrode system such as a bipolar system composed of a working electrode and a counter electrode; and a tripolar system composed of a working electrode, a counter electrode and a reference electrode. The solution may be sent from one to another among the chambers, for example, using a centrifugal force or a pressure applied to the channels with a pump.

Hereinafter, the present invention is described further in detail using examples.

COMPARATIVE EXAMPLE 1

Immobility of reagents concerned with the enzymatic cyclic reaction illustrated in FIG. 4 such as potassium ferricyanide, diaphorase, sodium malate, malic acid, potassium malate, NADP and malate dehydrogenase on a substrate was studied as described below. Polyethylene terephthalate (PET) substrates were used for the substrate.

The following solutions were prepared: 1 μL of 1M potassium ferricyanide aqueous solution obtained by dissolving potassium ferricyanide (manufactured by Wako Pure Chemical Industries, Ltd.) in pure water; 6.7 μL of 1000 U/mL diaphorase solution obtained by dissolving diaphorase (manufactured by UNITIKA LTD.) in 50 mM phosphate buffer (pH 7.5); 7.8 μL of 4M sodium malate aqueous solution obtained by dissolving sodium malate (manufactured by Wako Pure Chemical Industries, Ltd.) in pure water; 7.8 μL of 4M malic acid aqueous solution obtained by dissolving malic acid (manufactured by Wako Pure Chemical Industries, Ltd.) in pure water; 7.8 μL of 4M potassium malate aqueous solution obtained by dissolving potassium malate (manufactured by KANTO CHEMICAL CO., INC.) in pure water; 1 μL of 5 mM NADP aqueous solution obtained by dissolving NADP (manufactured by ORIENTAL YEAST Co., Ltd.) in pure water; and 1 μL of 25000 U/mL malate dehydrogenase solution containing malate dehydrogenase dissolved in 50% of glycerol (manufactured by Roche Diagnostics, Inc.).

Each solution was dropped on a PET substrate and then vacuum dried at room temperature for two hours. Table 1 shows the status of each solution after the drying, and immobility of each component mentioned above, from potassium ferricyanide to malate dehydrogenase.

TABLE 1

| | status after drying | immobility |
|---|---|---|
| potassium ferricyanide aqueous solution | completely desiccated | strong |
| diaphorase solution | completely desiccated | strong |
| NADP aqueous solution | completely desiccated | strong |
| sodium malate aqueous solution | highly viscid | strong |
| malic acid aqueous solution | almost completely desiccated | strong |
| potassium malate aqueous solution | highly viscid | strong |
| malate dehydrogenase aqueous solution | not dried | not immobilized |

As shown in Table 1, the potassium ferricyanide aqueous solution, the diaphorase solution and the NADP aqueous solution were completely desiccated through the drying. The sodium malate aqueous solution and the potassium malate aqueous solution were not completely desiccated but became highly viscid through the drying. The malic acid aqueous solution was almost completely desiccated through the drying. The components of potassium ferricyanide to potassium malate were immobilized strongly on the substrate. The malate dehydrogenase aqueous solution was hardly dried by the drying and thus the malate dehydrogenase contained in the solution was not immobilized on the substrate. The expression "immobilized strongly on the substrate" as used herein means a condition in which a reagent remains on the PET substrate even after centrifuging the substrate that has the reagent dropped and dried thereon at 1000 rpm for five seconds, and the expression "not immobilized on the substrate" means a condition in which the centrifuging removes the reagent from the substrate.

Thus, it is difficult to immobilize malate dehydrogenase on a substrate by dropping and drying a glycerol solution containing malate dehydrogenase on a substrate.

COMPARATIVE EXAMPLE 2

Immobility of malate dehydrogenase on a substrate was studied with mixed solutions A to C.

The mixed solution A was obtained by mixing a malate dehydrogenase solution and a potassium ferricyanide aqueous solution that were prepared in the same manner as Comparative Example 1. The mixed solution B was obtained by mixing a malate dehydrogenase solution and a diaphorase solution that were prepared in the same manner as Comparative Example 1. The mixed solution C was obtained by mixing a malate dehydrogenase solution and a NADP aqueous solution that were prepared in the same manner as Comparative Example 1.

The mixed solutions A to C were dropped on PET substrates and vacuum dried at room temperature for two hours. Table 2 shows the status of each solution after the drying, and immobilities of each malate dehydrogenaze contained in the solutions. These conditions according to mixed solutions D to F were also shown in Table 2.

TABLE 2

|  |  | status after drying | immobility |
|---|---|---|---|
| Comparative Example 2 | mixed solution A | not dried | not immobilized |
|  | mixed solution B | not dried | not immobilized |
|  | mixed solution C | not dried | not immobilized |
| Example 1 | mixed solution D | highly viscid | strong |
|  | mixed solution E | completely desiccated | strong |
|  | mixed solution F | highly viscid | strong |

As shown in Table 2, the mixed solutions A to C were not completely desiccated and did not become highly viscid through the drying. Thus, it is difficult to immobilize malate dehydrogenase on a substrate by dropping and drying mixed solutions A to C on a substrate.

EXAMPLE 1

Immobility of malate dehydrogenase on a substrate was studied with mixed solutions D to F.

The mixed solution D was obtained by mixing a malate dehydrogenase solution and a sodium malate aqueous solution that were prepared in the same manner as Comparative Example 1. The mixed solution E was obtained by mixing a malate dehydrogenase solution and a malic acid aqueous solution that were prepared in the same manner as Comparative Example 1. The mixed solution F was obtained by mixing a malate dehydrogenase solution and the potassium malate aqueous solution that were prepared in the same manner as Comparative Example 1.

The mixed solutions D to F were dropped on PET substrates and vacuum dried at room temperature for two hours. As shown in Table 2, the mixed solutions D and F were not completely desiccated but became highly viscid through the drying. The mixed solution E was completely desiccated through the drying. The malate dehydrogenase was immobilized strongly on the substrate through dropping and drying the mixed solutions D to F on the substrate. The known biosensors (for example, Bio Flow (BF-4) manufactured by Oji Scientific Instruments Co., Ltd.) can specify that malate dehydrogenase immobilized on a substrate is derived from a glycerol solution containing malate dehydrogenase.

Enzymatic activity of each malate dehydrogenase immobilized on the substrates through the drying of the mixed solutions D to F was studied. Reaction solutions were prepared by adding 13.7 µL of solutions obtained by mixing a potassium ferricyanide aqueous solution, a diaphorase solution, and a NADP aqueous solution that were prepared in the same manner as Comparative Example 1 with 5 µL of 1-M Tris-HCl (pH 9) and 10 µL of solutions of alkaline phosphatase labeled CRP antibodies, to the mixed solutions D to F immobilized on the PET substrates. The concentrations of the alkaline phosphatase labeled CRP antibodies in the reaction solutions were 0 M, 0.083 nM, 0.415 nM, and 0.830 nM.

Figure 7:
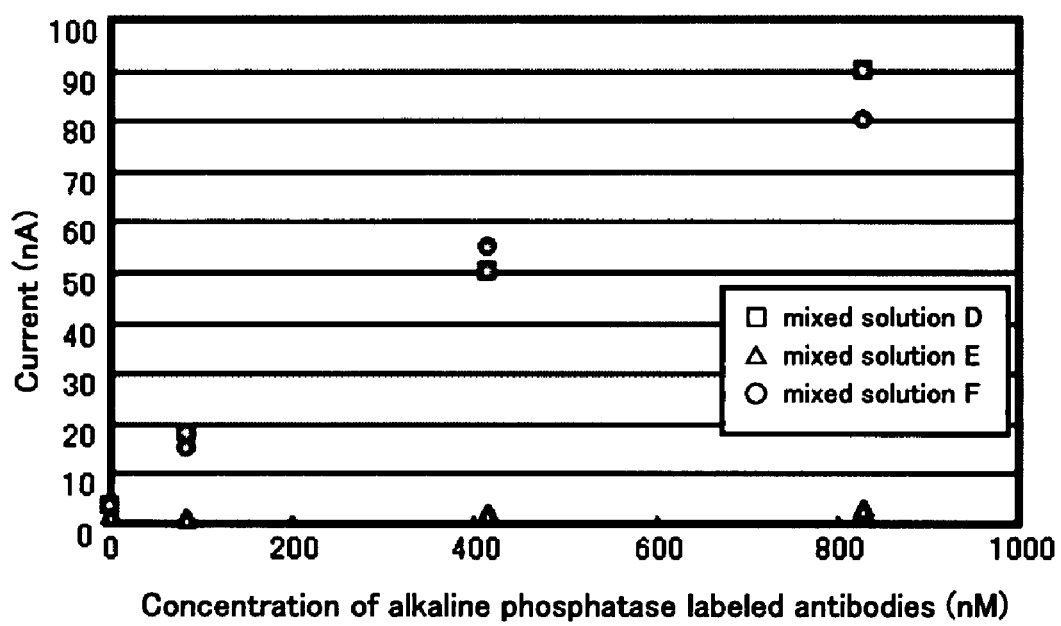
FIG. 7 is a graph illustrating the result of potentiometry obtained in Example 1.

Each reaction solution was incubated at 30° C. for ten minutes, and then a constant voltage of 400 mV was applied to each solution for performing the potentiometry. FIG. 7 is a graph illustrating the relationship between the concentration of the alkaline phosphatase labeled CRP antibodies in the reaction solution and the amount of current flowed in each reaction solution directly after the voltage application. As illustrated in FIG. 7, in the reaction solutions prepared with the mixed solutions D and F, the amount of current and the concentration of the alkaline phosphatase labeled CRP antibodies were highly correlated, and thus the malate dehydrogenase was not inactivated. The malate dehydrogenase in the reaction solution prepared with the mixed solution E was less active than that in the solutions prepared with the mixed solution D and F.

As explained above, malate dehydrogenase can be immobilized strongly on a substrate without inactivation by using a mixed solution that is obtained by adding malate such as potassium malate and sodium malate to a glycerol solution containing malate dehydrogenase. Although enzymatic activity of malate dehydrogenase might be decreased, malate dehydrogenase can be immobilized strongly on a substrate also using a mixed solution that is obtained by adding malic acid to the glycerol solution.

INDUSTRIAL APPLICABILITY

The present invention provides a method of immobilizing malate dehydrogenase on a substrate with a glycerol solution containing malate dehydrogenase. Hence, the present invention has a great deal of potential in each field where the immunoassay is required to be performed on a biosensor chip.

What is claimed is:

1. A method of immobilizing malate dehydrogenase on a substrate, the method comprising:
    placing a mixed solution on a substrate, the mixed solution being obtained by adding at least one selected from malic acid and malate to a glycerol that contains malate dehydrogenase; and
    drying the mixed solution to immobilize the malate dehydrogenase on the substrate.

2. The method according to claim 1, wherein the malate includes at least one selected from potassium malate and sodium malate.

3. The method according to claim 1, wherein the mixed solution is obtained by adding the malate to the glycerol.

* * * * *